(12) United States Patent
Odegard et al.

(10) Patent No.: US 7,660,678 B2
(45) Date of Patent: Feb. 9, 2010

(54) ON-SITE METHOD OF PROVIDING ANALYSIS OF POTENCY AND PURITY OF PHARMACEUTICAL COMPOUNDS

(75) Inventors: Russell David Odegard, Eureka, MO (US); Earl Michael Pruett, St. Louis, MO (US); John Peter Coates, Newtown, CT (US)

(73) Assignee: MedPro Holdings, LLC, St. Louis, MO (US)

( * ) Notice: Subject to any disclaimer, the term of this patent is extended or adjusted under 35 U.S.C. 154(b) by 0 days.

(21) Appl. No.: 11/726,417

(22) Filed: Mar. 22, 2007

(65) Prior Publication Data

US 2007/0239367 A1 Oct. 11, 2007

Related U.S. Application Data

(63) Continuation-in-part of application No. 11/051,419, filed on Feb. 4, 2005, now Pat. No. 7,197,405.

(60) Provisional application No. 60/541,995, filed on Feb. 5, 2004.

(51) Int. Cl.
*G01N 31/00* (2006.01)
(52) U.S. Cl. .............................. 702/30; 702/27; 356/51
(58) Field of Classification Search .................. 702/22, 702/27, 28, 30, 32, 127; 250/339.07, 371, 250/301, 339.12, 390.07; 356/51, 70, 239.6
See application file for complete search history.

(56) References Cited

U.S. PATENT DOCUMENTS

| | | | |
|---|---|---|---|
| 5,078,135 A * | 1/1992 | Caprioli ..................... 600/309 |
| 5,451,572 A * | 9/1995 | Cipolla et al. ................. 514/21 |
| 5,691,701 A | 11/1997 | Wohlstein et al. |
| 6,549,861 B1 | 4/2003 | Mark et al. |
| 6,618,138 B2 | 9/2003 | Khoury |
| 6,667,802 B2 | 12/2003 | Faus et al. |
| 6,765,212 B2 | 7/2004 | Goetz et al. |
| 6,771,369 B2 * | 8/2004 | Rzasa et al. .................. 356/326 |
| 6,853,447 B2 | 2/2005 | Goetz |
| 7,006,214 B2 | 2/2006 | Rzasa et al. |
| 7,057,722 B2 | 6/2006 | Gehrlein et al. |
| 7,396,650 B2 * | 7/2008 | Perraut et al. ................. 435/7.1 |

(Continued)

OTHER PUBLICATIONS

DYNA Labs, Welcome to Dynalabs at http://www.dynalabs.us. Copyright @ Nov. 15, 2004 (4 pages).

(Continued)

*Primary Examiner*—Manuel L Barbee
(74) *Attorney, Agent, or Firm*—Polster Lieder Woodruff & Lucchesi, LC

(57) ABSTRACT

A computer facilitated method of requesting a spectral analysis of a sample having an unknown concentration or purity, performing an energy absorption analysis of the sample to obtain spectral data regarding the analysis and comparing the spectral data to a stored spectral data regarding the analyses of the samples having a predetermined concentration and purity to determine the concentration or purity of the sample having an unknown concentration or purity. The spectral analysis is performed on site where the sample is prepared or administered using a portable analytical apparatus and provides a real time report of the concentration or purity of the sample. The apparatus requires only a small sample size.

22 Claims, 8 Drawing Sheets

U.S. PATENT DOCUMENTS

| | | | |
|---|---|---|---|
| 2001/0044730 A1* | 11/2001 | D'Silva | 705/3 |
| 2002/0108892 A1 | 8/2002 | Goetz et al. | |
| 2003/0009385 A1 | 1/2003 | Tucciarone et al. | |
| 2003/0128804 A1 | 7/2003 | Poteet et al. | |
| 2003/0168585 A1 | 9/2003 | Wall | |
| 2004/0155202 A1 | 8/2004 | Poteet et al. | |
| 2005/0077476 A1 | 4/2005 | Poteet et al. | |
| 2005/0130881 A1* | 6/2005 | Shashoua | 514/8 |
| 2006/0160784 A1* | 7/2006 | Magda et al. | 514/185 |

OTHER PUBLICATIONS

ValiMed website; www.valimed.com ; Copyright @ 2004 CDEX, Inc.; (3 pages).

* cited by examiner

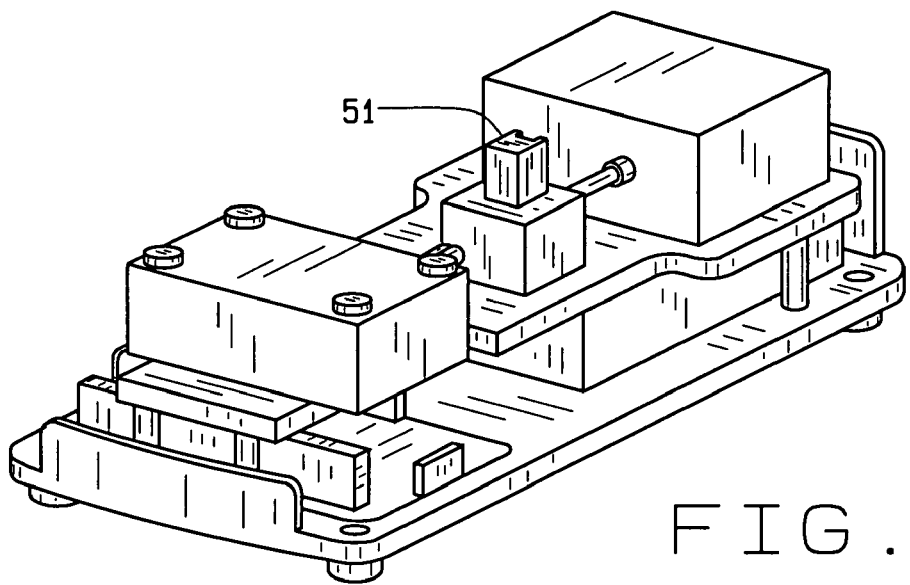
FIG. 8
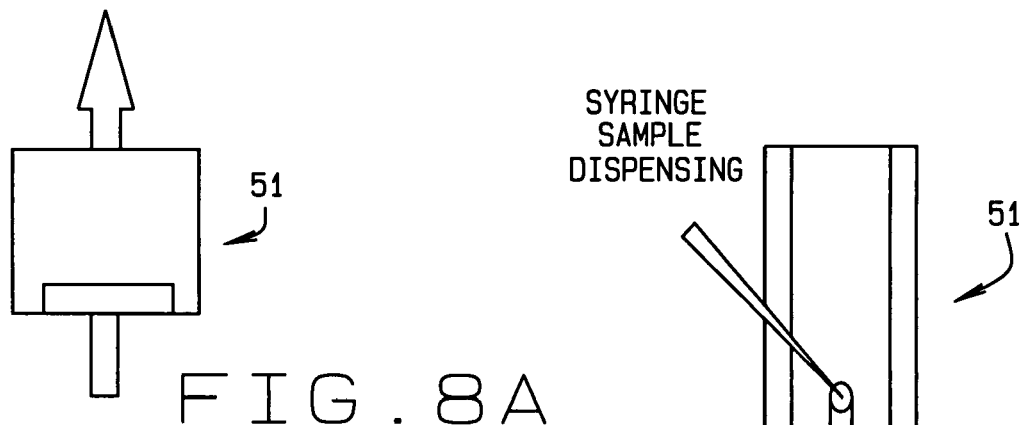
FIG. 8A
FIG. 8B
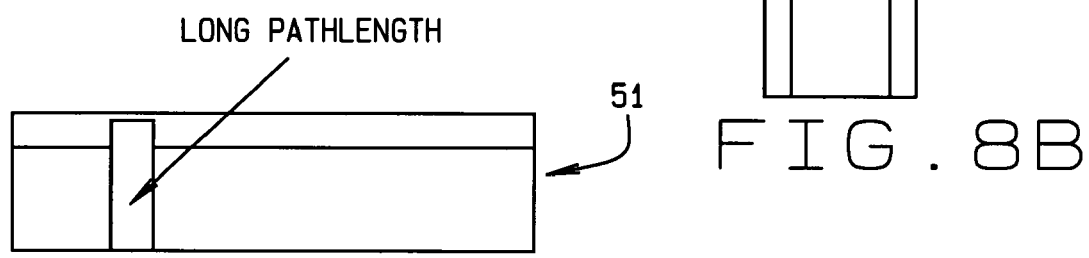
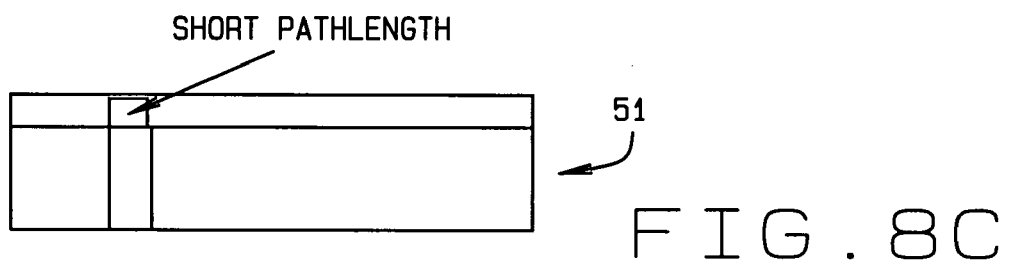
FIG. 8C

QUARTZ CELL
a = UV-vis PATHLENGTH
b = NIR PATHLENGTH

A = SAMPLE
B = SPECTRAL SEPARATION DEVICE
C = DETECTOR SYSTEM (CAN BE AN ARRAY)

GENERIC SPECTRAL MEASUREMENT SYSTEM

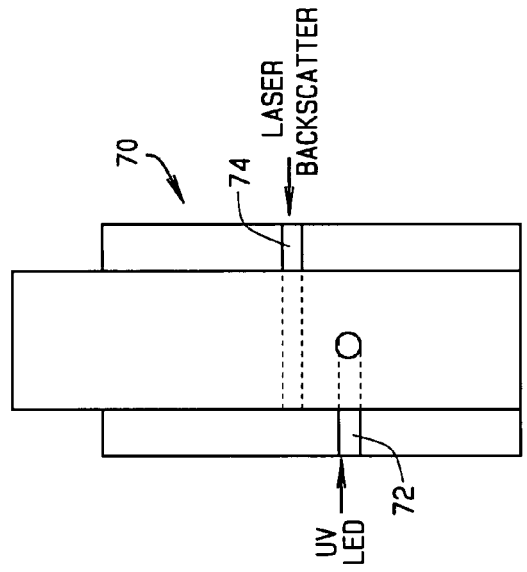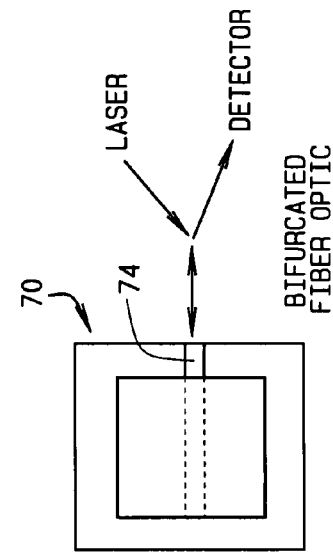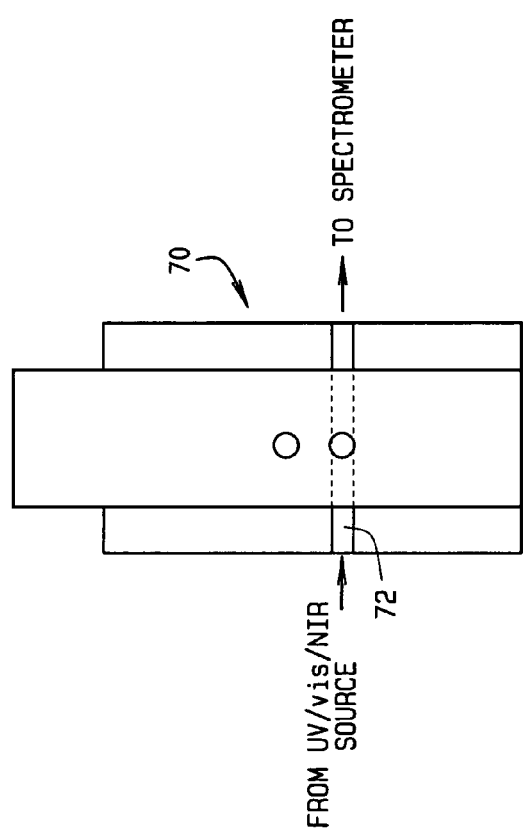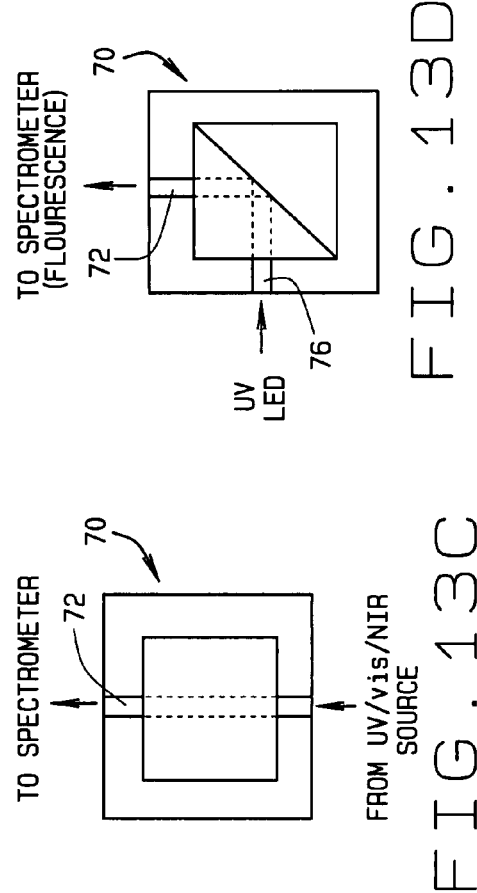

ON-SITE METHOD OF PROVIDING ANALYSIS OF POTENCY AND PURITY OF PHARMACEUTICAL COMPOUNDS

CROSS REFERENCE TO RELATED APPLICATIONS

This application is a continuation-in-part of application Ser. No. 11/051,419 filed Feb. 4, 2005, now U.S. Pat. No. 7,197,405, which claims the benefit of provisional patent application Ser. No. 60/541,995, filed Feb. 5, 2004, both of which are incorporated herein by reference.

BACKGROUND OF THE INVENTION

This invention relates to methods of verifying the identity and determining the concentration, potency, purity and presence of contaminants, including, but not limited to, microbial, endotoxins and particulate matter in a mixture of ingredients on site in a healthcare facility, pharmacy, home care situation, pharmaceutical manufacturing facilities and other sites, as well as series of integrated devices, systems and processes for the analysis, organization, monitoring and reporting of such analyses and related metadata through an electronic network.

Pharmacies generally compound pharmaceuticals that are not readily available on the market, for example, but not limited to, specialized dosage forms, certain oncological formulations, pediatric formulations, certain ophthalmic preparations, intravenous solutions, or other compounded pharmaceuticals referred to as compounded sterile preparations ("CSPs"). In the past, the pharmacists generally followed good compounding practices mandated by federal and state pharmacy practice acts and accepted professional compounding techniques. However, these CSPs have not been subject to concentration and purity guidelines set forth by the United States Food and Drug Administration ("FDA") or other regulatory bodies. If a compounding pharmacy wanted to analyze a product for potency or purity, it was required to engage outside testing laboratories that employed traditional analysis such as chromatography or other analytical procedures to test the individual CSPs. These processes are costly and time consuming and employed only on a limited basis.

It recently has been determined that some pharmacies have failed to meet the concentration guidelines set forth by the prescribing physician, or have produced pharmaceuticals having impurities, microbial, endotoxin and particulate matter. In response, the regulatory bodies have set forth guidelines requiring that extemporaneous CSPs prepared under high-risk conditions be tested for concentration and purity prior to distribution to ensure the safety of the pharmaceutical for public use. Moreover, it is anticipated that in the future, regulatory bodies will set forth compounding guidelines for all CSPs, regardless of risk.

While the guidelines set forth by the regulatory bodies have resulted in safer and more reliable CSPs, the testing of each batch or individual CSP using traditional physical analyses has resulted in a loss of time and financial resources for the pharmacies. Furthermore, traditional physical analysis takes time and is not necessarily useful in emergency situations.

Also, the need often arises for a CSP or other admixed compound to be extemporaneously prepared at or near the time for administration, leaving little time for conventional analysis of the product. For example a physician or nurse may be required to compound a product in a patient care area.

Therefore, there is a need for methods and systems, including procedures, hardware and software, for testing CSPs and other admixed compounds that avoid the expense, time and other problems associated with the use of traditional physical analyses for testing CSPs. It would be advantageous to have such methods and systems that allow for the testing on-site, for example in patient care areas of healthcare facilities, at a pharmacy where the CSP is prepared or both. In facilitating such a method, it would be advantageous to have an instrument for performing at least part of such analysis that is fully functional, but small enough to be portable or even handheld and uses only a small sample volume.

SUMMARY OF THE INVENTION

One aspect of the invention is a method of analyzing a sample taken from a CSP or other compounded product having a desired concentration or purity at the site of preparation and/or administration of the product to verify the concentration or purity of the sample prior to administration of the product to a subject. The invention can employ a portable analytical instrument that can analyze small volume samples.

BRIEF DESCRIPTION OF THE DRAWINGS

FIG. 8 is a perspective view of the inner structures of the portable instrument of FIG. 7;

FIG. 8A is a top plan view of an example sample slide structure of the present invention;

FIG. 8B is a side elevational view thereof; and

FIG. 8C is an end plan thereof.

FIG. 13A is a front plan view of another embodiment of a sample slide and sample holder of the present invention;

FIG. 13B is a front plan view of another embodiment of a sample slide and sample holder;

FIG. 13C is a top plan view of a sample slide and sample holder;

FIG. 13D is a top plan view of another sample slide and sample holder;

FIG. 13D is a top plan view of a sample slide and sample holder of the present invention; and FIG. 13E is another top plan view thereof.

DETAILED DESCRIPTION OF THE INVENTION

Figure 1:
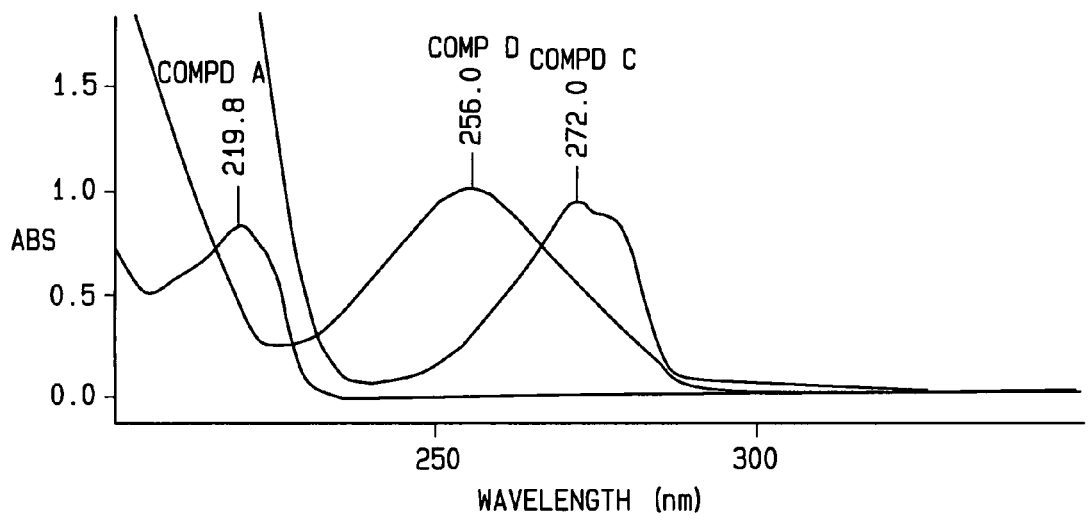
FIG. 1 is a graph illustrating example UV light absorbance spectra of three different compounds.

New and useful methods for verifying the identity and determining or confirming the presence of a target or active ingredient as well as potency, purity and presence of contaminants, microbial, endotoxin and particulate matter (referred to hereinafter as "purity") in a mixture of ingredients, and a series of integrated systems and processes for the requesting, performing, organizing, monitoring and reporting of such analyses and related metadata through an electronic network are provided.

In various aspects of the invention, the term product producer is anyone or any entity that produces a CSP or other compounded product comprising an extemporaneously compounded or admixed ingredients having a desired or intended concentration or purity that is analyzed as if it has an unknown concentration or purity so as to confirm or verify that the sample does indeed comprise the desired or intended concentration or purity.

In the various aspects of the invention, the requester or user includes one who prescribes or administers the product to a recipient of the sample. It will be understood that in certain aspects of the invention, the user also can be a product producer.

In another aspect of the invention the method comprises the product producer producing a product having a desired concentration or purity; performing an analysis of a product having a desired concentration or purity; obtaining data regarding the analysis of the product having a desired concentration or purity; storing the data in a retrievable form; user receiving the product from the product producer; the user performing an analysis of the product; the user obtaining data regarding the analysis of the product; the user comparing the data regarding the analysis of the product to the data regarding the analysis of the product having a desired concentration or purity which was stored in a retrievable form by the product producer; the user confirming the desired concentration or purity of the product through the comparison; and user administering or not administering the product to a recipient based upon the comparison.

In one aspect of the invention, conducting the analysis of the samples by the user comprises comparing the analytical data obtained from the analysis of the product with historical analytical data regarding analyses of samples having a known concentration or purity stored in the database by the product producer or a service provider. The analytical data includes a library of predetermined ranges of concentration or purity. The predetermined ranges can be expressed as spectra based upon spectral data obtained through spectral analysis of samples having known concentrations or purities. The library may include, but is not limited to pharmaceutical, organic or biochemical materials spanning a normal process range.

In one aspect of the invention, the analyses are spectral analyses to determine energy absorbance by the contents of the samples.

In one aspect of the invention, the method and system of the invention integrate the use of near-infrared ("NIR") energy absorption technology within an electronic system and business process for maintaining the results of the analyses for future use. The analysis of samples is conducted using NIR energy absorption technology.

In one aspect of the invention, the method and system of the invention integrate the use of ultraviolet-visible (UV-vis) light absorption technology within an electronic system and business process for maintaining the results of the analyses for future use. The analysis of samples is conducted using UV-vis light absorption technology.

In one aspect of the invention, the method and system of the invention integrate the use of any combination of NIR energy absorption technology and ultraviolet-visible (UV-vis) light absorption technology within an electronic system and process for maintaining the results of the analyses for future use. The sample analysis is conducted using any combination of NIR energy absorption and UV-vis light absorption technology. These technologies may reflect information from the active ingredients. The excipients and diluents and solvents. As indicated the spectral region will include the visible spectral regions, and so any spectral contributions from color centers will be included.

In one aspect of the invention fluorescence signatures are used to detect active ingredients that have strong fluorescence signatures and also for detecting contamination.

In one aspect of the invention, the analysis of the sample is monitored before, during and after the analysis. The results are generally integrated into a broader database that comprises a library of acceptable ranges expressed as spectra derived from spectral analyses. The spectral analyses can be performed by UV light absorption technology, NIR energy absorption technology, visible light absorption technology or a combination thereof. Furthermore, the analysis can be performed by other technologies such as fluorescence, nephelometry, turbidity, laser light scattering, DNA sequencing, Raman, mid-infrared (IR), TD-NMR, TeraHertz, x-ray or so forth. The integration of the systems into a larger body of data and results enables future use of the data and results for further analysis.

In one aspect of the invention, the database, which includes the results of the analyses, as well as other data, will be hosted on a web server or other similar communication network component, which will permit the product producer or the user or both to access the system from a remote site and perform certain methods of the invention.

In one aspect of the invention, the database, which includes the results of the analyses, as well as other data, will be hosted on the analytical instrument which will permit the product producer or the user or both to access the system from a remote site and perform certain methods of the invention.

In one aspect of the invention, samples are analyzed for concentration and purity. More specifically, samples, which may comprise pharmaceuticals, are analyzed for concentration, as well as to determine if they are sufficiently pure, to establish whether the pharmaceuticals fall within parameters set forth by the regulatory bodies. Specifically, the desired concentration of a target or active ingredient as well as presence or concentration of pathogens or other contaminants is determined using traditional physical analytical techniques, as well as UV-vis light absorption or NIR energy absorption technology which produce spectral data that can be stored electronically for later comparison to other spectral data. The results of both analyses are added to a database for future use, which also contains the concentration and purity parameters set forth by the regulatory bodies.

In one aspect of the invention, the database is continually expanding.

In various aspects and embodiments of the invention, the sample to be analyzed is a compounded sterile preparation ("CSP") or non-sterile preparation.

One aspect of the invention comprises apparatus that can perform an analysis of a sample at the site of preparation or administration of the sample. The apparatus can perform a UV, NIR, visible light or other qualitative or quantitative analysis of the sample and communicate the analysis to a computer comprising a database of spectral data that has been stored electronically. The apparatus is operatively associated with the computer and database by electronic or by wireless communications or any type of data transmission technology, including the Internet, whether now known or unknown.

In one aspect of the invention the apparatus performing the analysis includes the database.

In one aspect of the invention, a product producer prepares an admixture of ingredients for administration to a subject, the admixture having a desired potency and purity. The product producer introduces a sample of the admixed ingredients into an apparatus that conducts a UV-vis, NIR, a combined UV-vis/NIR analysis, or a combination of UV-vis and/or NIR with another spectral measurement technology, of the admixture to obtain spectral data. The spectral data is transmitted to a computer database of previously determined spectral data, generally maintained by the product producer or a service provider. The appropriately programmed computer compares the spectral data, the results of the comparison confirming the potency and purity of the admixture. The admixture is forwarded to a user for administration to a recipient. The user then introduces a sample of the admixed ingredients into a portable apparatus that also conducts a UV, NIR, or combined UV/NIR analysis, or a combination of UV and/or NIR with another spectral measurement technology, of the sample to obtain spectral data. The spectral data is transmitted to the computer database of previously determined spectral data. An appropriately programmed computer compares the spectral data transmitted from the portable apparatus, the results of the comparison confirming the potency and purity of the user's sample. The results of the analysis are communicated to the portable apparatus for access by the user.

In one aspect of the invention the apparatus used for the measurement also features a special sample holder that accepts sample slides that are optimized for light throughput and minimization of sample consumption. The holder has the option to include two optical channels. The optical channels hold the sample to be analyzed and the length of the optical channel can be referred to as the path length. One of the channels provides the option to excite the sample with a specific wavelength normal to the analytical channel and to measure fluorescence of the sample within the analytical channel. This fluorescence may be native to the sample and may be characteristic of materials used in the admixture. Alternatively, the fluorescence may be induced by the addition of a specific chemical reagent that is added for the purpose of inducing fluorescence as a consequence of the presence of one or more endotoxins or similar biological agents or microbials. The reagent added is specific and provides a unique fluorescence (resulting in one or more emissions of specific wavelengths). The spectral analysis of the signatures produced is used to characterize the target agents contained in the sample plus the concentration of the target agents.

An additional second optical channel mounted normal to the analytical channel features a laser back scatter assembly comprising of a bifurcated fiber optic cable featuring laser excitation in one channel and optical emission detection as a result of particulate backscatter in the return fiber channel. This configuration provides information on the presence of particulate matter. The apparatus features a sampling block that provides access to the three channels defined, i.e. a main analytical channel (used for UV-vis-NIR), a fluorescence excitation channel and a laser illuminated channel to enable all three modes of operation. A combination of the spectral data, the induced fluorescence data and the particulate data enables the apparatus to provide a full signature of dosage potency and purity for any given sample.

In one aspect of the invention, a product producer prepares an admixture of ingredients for administration to a subject, the admixture having a desired potency and purity and transports the admixture to a user for administration to a recipient. The user introduces a sample of the admixed ingredients into a portable apparatus that conducts a UV-vis, NIR, combined UV-vis/NIR analysis, or a combination of UV-vis and/or NIR with another spectral measurement technology, of the sample to obtain spectral data. The spectral data is transmitted to a computer database of previously determined spectral data, generally maintained by the product producer or a service provider. The appropriately programmed computer compares the spectral data transmitted from the portable apparatus, the results of the comparison confirming the potency and purity of the sample. The results of the analysis are communicated to the portable apparatus for access by the user. In one aspect of the invention, the portable apparatus includes the computer, the database or both.

In one aspect of the invention, a user prepares the admixture of ingredients for administration to a subject at or near the site of administration, the admixture having a desired potency and purity. A sample of the admixed ingredients is introduced into a portable apparatus by the user that conducts a UV-vis, NIR, combined UV-vis/NIR analysis, or a combination of UV-vis and/or NIR with another spectral measurement technology, of the sample to obtain spectral data. The spectral data is transmitted to a computer database of previously determined spectral data. The appropriately programmed computer compares the spectral data transmitted from the portable apparatus, the results of the comparison confirming the potency and purity of the sample. The results of the analysis are communicated to the portable apparatus for access by the user. The appropriately programmed computer can be separate from the portable apparatus or the portable apparatus may comprise the appropriately programmed computer or database or both.

In another aspect of the invention a method of performing an analysis of a sample having a predetermined concentration and purity, obtaining data regarding the analysis of the sample having a predetermined concentration and purity, storing the data in a retrievable form, performing an analysis of a sample having an unknown or desired concentration and/or purity, obtaining data regarding the analysis of the sample having an unknown or desired concentration and/or purity at the, comparing the data regarding the analysis of the sample having an unknown concentration and/or purity to the data regarding the analysis of the sample having a predetermined concentration and purity which was stored in a retrievable form; and determining a concentration and/or purity of the sample having an unknown or desired concentration and purity through the comparison. Steps of the invention can be conducted at a central location where the medication is compounded, or at a remote site where the patient is located, or both.

In one aspect of the invention, the analysis is performed using a system comprising a portable apparatus comprising appropriate spectral measurement technology that runs the analysis and transmits data to an appropriately programmed computer including central database of known data for comparison. In other aspects of the invention, the portable instrument can include an appropriately programmed computer and its own database of known data for comparison.

The data obtained through the analysis can be conducted or transmitted as desired by electronic means, including, but not limited to, a localized screen, telephone systems, wireless communication systems, or data delivery systems of any type, including the Internet, whether presently known or unknown.

One aspect of the invention provides a quality control system that records the quality and identity of a medication produced at a centralized location, such as a hospital pharmacy, and then further confirms that the medication dispensed to a patient is the correct medication at the correct dosage and purity. One representative embodiment of this aspect of the invention provides for identifying data, such as a spectral signature of a medication on a spectral measurement system located at the pharmacy. The spectral signature is recorded on an instrument that incorporates multi-level spectral measurements that include measurements made in the ultraviolet (UV), visible, or near infrared (NIR) spectral regions. For reference, these spectral regions are defined as covering the following wavelength regions: 200 nm to 400 nm (UV), 400 nm to 700 nm (visible), and 700 nm to 2500 nm (NIR). The UV and Visible are commonly combined and referenced as UV-vis, where a single measurement can be made with a common measurement technology. The spectral signature information is stored within a database. When a prescription is produced for a patient, the patient is assigned a patient identifier. The spectral signature of the prescribed medication is determined and through the patient identifier the spectral signature of the prescribed medication is linked to that specific patient. The patient identifier and the spectral signature of the prescribed medication are compared to the stored spectral signature to confirm that the right patient is receiving the correct medication.

Another aspect of the invention provides a system for the confirmation of the delivery of a correct medication and dosage to a patient is made at a remote location, such as the bedside of a patient using a portable apparatus operated by the individual, for example the nurse administering the medication. The portable apparatus duplicates the measurement made in the pharmacy, and compares the resultant spectral signature with the spectral signature of the medication assigned to that patient that is stored in the database. A matching algorithm is used to compare the two sets of spectral data. With a match within defined limits of tolerance, the portable apparatus will signal to the individual, in real time, that it is acceptable to administer the medication to the patient. Conversely should the signatures not match, the portable apparatus will signal to the individual that the medication is not acceptable to administer to the patient.

In one aspect, the invention comprises two sets of hardware and generally one software program. For example, there is a central or master unit in the pharmacy. This unit may comprise a spectral measurement technology, a computer and a database. This is a multifunctional unit that includes the same spectral measurement technology that produces the spectral signatures and also does purity related testing for particulates and bacteria. The central unit uses small sampling for example a micro sample slide, to minimize sample consumption.

This aspect of the invention also includes a portable apparatus. The portable apparatus and the master unit in the pharmacy include the same spectral measurement technology and are operated with same master software to provide identical data acquisition and data processing. The pharmacy unit typically is used to generate the library spectra that are used for reference purposes. However, if required, portable unit can also be used for this purpose. The spectral engines of the two system, the master unit and the portable apparatus are identical. The same software is used on all sets of data irrespective of which unit generates the data. In this way the spectra from the portable apparatus can be compared with the spectral data produced on the master unit. The software provides for spectrum standardization and mobility.

The software includes a method development aspect that applies to both the master system and the portable apparatus. When a method is developed on the master system and downloaded into the portable apparatus, the portable apparatus computer runs the method when selected in a runtime mode. The method is protected and cannot be altered by the user, which provides for uniformity and quality assurance. The method defines the steps taken in the analysis including how the spectral data are acquired and processed and how results are reported. When operated, the portable apparatus has its own set of menus that guide the user through the analysis. These are also defined by the method. Options for storage and spectral data transfer between systems are also included.

The methods of the invention can be utilized to eliminate the time consuming task of testing each compounded product that is produced by a pharmacy or user, as examples, using traditional physical analysis, which reduces the time between the preparation of the compounded product and its administration, and medication errors.

According to one aspect of the invention, once a particular admixture is analyzed using traditional physical analysis, NIR technology, UV-vis technology or other applicable technology, the same admixture can simply be tested for compliance with the regulatory bodies' concentration or purity parameters using UV-vis or NIR technology, or another relevant spectral measurement technology, which is much less labor intensive and time consuming when compared to traditional physical analysis. The spectral data stored in the database from the initial UV-vis or NIR analysis is compared to the spectral data gathered from the sample being tested using UV-vis or NIR technology, or another relevant spectral measurement technology.

In the various aspects of the invention, the spectral data is used to develop an equation or an appropriate calibration function that is then used to calculate the concentration of a sample based upon the absorbance of the sample at a predetermined wavelength in nanometers (nm) or wave number in reciprocal centimeters ($cm^{-1}$), as explained below, or other appropriate units of measurement.

By way of further example, an electronic database of spectral data is established using the results of analysis of samples of known concentration or purity. This spectral data can be obtained by using UV-vis light absorption technology, NIR energy absorption technology or both, or another relevant spectral measurement technology.

Generally, UV-vis technology is used to determine the spectral data of samples having low concentrations of constituents, for example, samples having an estimated concentration of less than approximately 10 mg/ml of active or target constituent that absorbs UV and/or visible light. One example of equipment used to perform a UV analysis is the Cary 50 manufactured by Varian, Inc., Palo Alto, Calif.

Those samples having an estimated concentration of greater than approximately 10 mg/ml may be analyzed by NIR technology. One example of equipment used for performing the NIR analysis is the Vector 22/N manufactured by Bruker Optics, Billerica, Mass. In general, UV-vis and UV-excited fluorescence (with visible detection) are methods of choice to obtain the spectral data from samples containing low concentrations of active ingredients. NIR is typically considered for use for high concentration measurements, and for measurements on the excipients/diluents in cases where the materials involved do not have a UV-vis signature.

FIGS. 1 through 4 illustrate graphs that reflect example UV spectra and NIR spectra. Both technologies can be used to identify and quantify a target ingredient or constituent of a sample. The respective graphs indicate energy (light) absorption as the vertical coordinate on the left (expressed as absorbance), and wavelength (usually expressed in nanometers, nm) or wave number ($cm^{-1}$) as the horizontal coordinate across the bottom. UV-vis spectra are normally presented in wavelength units, whereas NIR spectra can be represented with either wavelength (nm) or wave number ($cm^{-1}$) formats. The use of wave number is often used for spectra recorded on FT-NIR (Fourier transform near infrared) instrumentation.

FIG. 1 illustrates UV absorbance spectra of three different compounds. As shown, Compound A exhibits maximum absorbance at a UV wavelength of 219.9 nm; Compound B exhibits maximum UV absorbance at 256.0 nm; and Compound C exhibits maximum UV absorbance at 272.0 nm. Hence, FIG. 1 illustrates the fact that three different compounds have three different, yet unique, UV absorption signatures.

Figure 2:
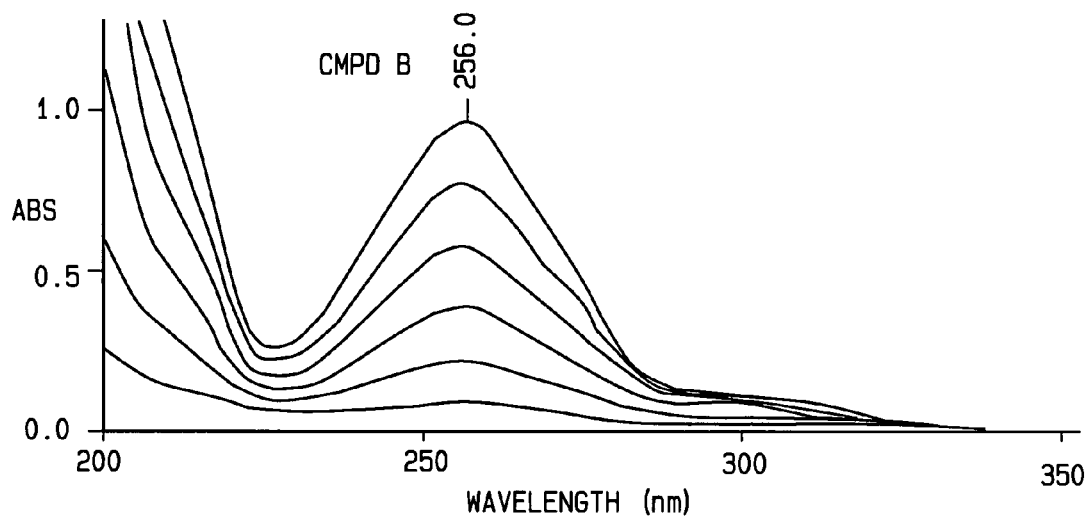
FIG. 2 is a graph illustrating example UV light absorbance spectra of six different concentrations of a single target constituent.

FIG. 2 Illustrates UV absorbance spectra of various concentrations of Compound B. In the illustrated graph, six (6) different concentrations of Compound B were analyzed. It will be noted that, despite the concentration of Compound B, maximum UV absorbance of each of the six samples occurs at 256.0 nm, confirming the presence of target constituent Compound B.

Figure 3:
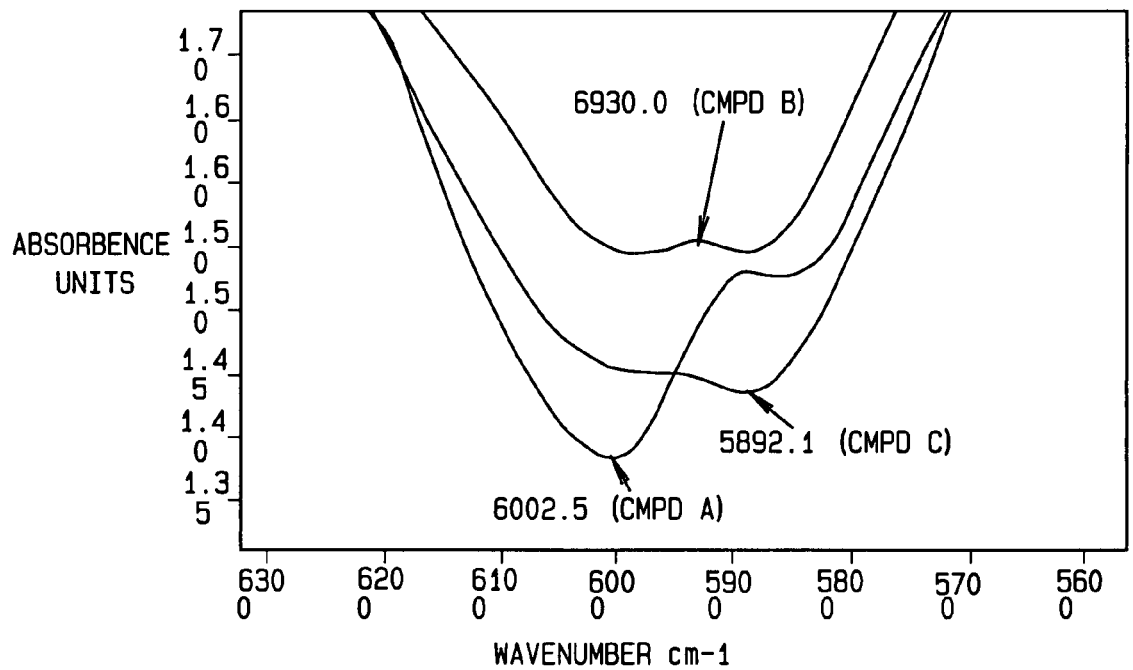
FIG. 3 is a graph illustrating example NIR energy absorbance spectra of three different compounds.
Figure 4:
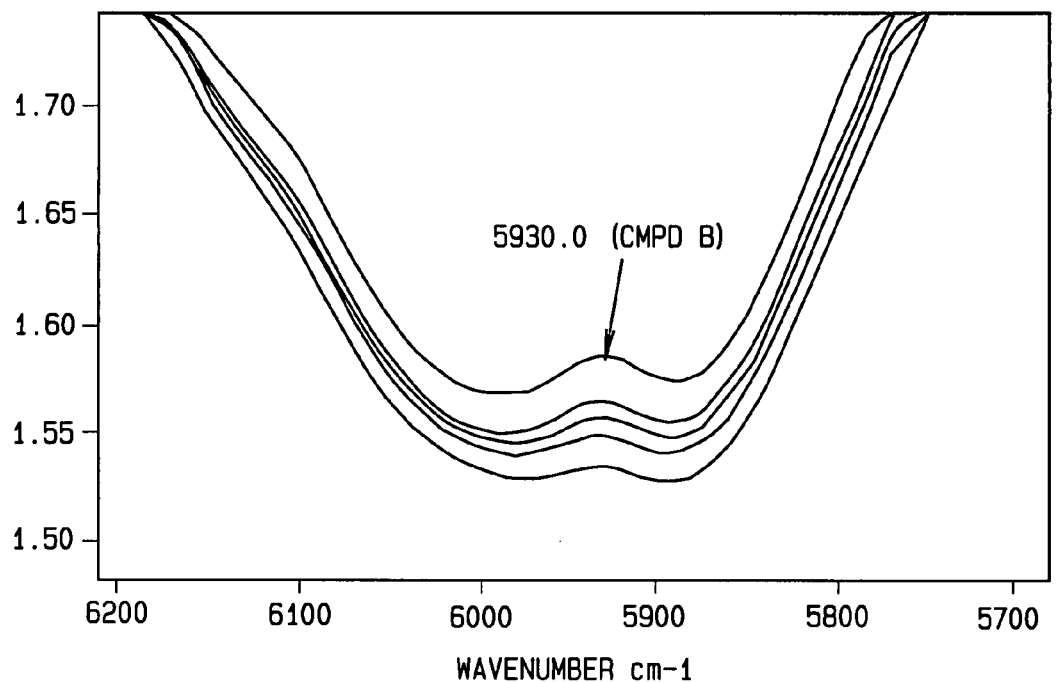
FIG. 4 is a graph illustrating example NIR energy absorbance spectra of six (please check this, it looks like five) different concentrations of a single target constituent of FIG. 2.

Similarly, FIGS. 3 and 4 illustrate example NIR energy absorbance spectra for Compounds A, B and C. As seen in FIG. 3, the maximum absorbance of Compound A occurs at 6002.5 $cm^{-1}$ (1666 nm) Compound B exhibits maximum absorbance at 5930.0 $cm^{-1}$ (1686 nm) and Compound C exhibits maximum absorbance at 5892.1 $cm^{-1}$ (1697 nm).

FIG. 4 illustrates the NIR absorbance spectra of Compound B. In FIG. 4, five (5) different dilutions of Compound B are analyzed, with maximum absorbance confirmed at 5930.0 $cm^{-1}$ (1686 nm).

In the context of present invention, both measurement regions can be used to identify and quantify a known compound. The choice of measurement region and appropriate spectral measurement technology used depends, for example, upon the concentration of the compound and the location of the absorbance peaks.

Generally speaking, in use, several concentrations are made of samples of known target constituent and purity. These samples having known target constituents and concentration are analyzed by the UV and/or NIR technology and absorbance spectra are obtained of the type illustrated by FIGS. 2 and 4. The NIR or UV absorbance peaks should correlate for each dilution. These spectral data are stored in a database.

Subsequent analyses are performed on samples of an expected target constituent having an unknown concentration or purity. Data in the form of absorbance spectra derived from diluted or undiluted samples having an unknown concentration or purity are obtained, also similar to those shown in FIGS. 2 and 4. Spectral data obtained by the subsequent analysis of samples of unknown concentration or purity can be compared to the spectral data stored in the database.

Using a suitable algorithm, an equation correlation function, or numerical relationship is derived from the spectra (in absorbance or derivative formats) using the absorbance value or a derivative thereof at single or multiple wavelengths (or wave numbers) and the known concentration value of each sample. The equation (function or relationship) is applied to the absorbance spectra (or derivative spectra) of the samples of unknown concentration, and the concentration of the target constituent(s) in the provided sample is (are) derived. Hence, a determination of the concentration or purity of the sample having an unknown concentration or purity is determined from the comparison of its spectral contributions (measured absorption functions) to the spectral contributions (measured absorption functions) of samples having known concentrations or purities and the application of the equation (function or relationship). The comparison, therefore, can include the step of applying the appropriate equation (function or relationship).

As can be appreciated from considering FIGS. 1 and 3, it is possible to identify and verify the target constituent. These spectra demonstrate that each compound has a unique absorption curve. The spectral contributions that are unique to any given compound, for example, can be considered to be a spectral fingerprint of that compound. As illustrated, FIGS. 1 and 3 show that Compounds A, B and C, for example, have their own spectral fingerprint. Consequently, if the sample of unknown concentration or purity includes a target constituent that is supposed to be Compound A, the analysis can confirm that the target constituent is indeed Compound A.

It will be appreciated that NIR analysis of appropriate samples has an advantage in certain circumstances over that of UV or UV-vis analysis. While both measurement techniques can provide a determination of concentration or purity of the target constituent of an unknown or unconfirmed concentration, the spectral data of the sample produced by NIR, may under certain circumstances be better used to identify the target constituent, as well as the concentration. That is, the spectral data produced by NIR is capable of providing a more specific spectral fingerprint that is unique to the target constituent. This primarily is a result of the fact that UV involves an electronic-transition (within a molecule) and there are a limited number of peaks due to specific "chromophores", such as a phenyl or benzene ring in the structure. NIR, however, involves vibrational transitions featuring all the atoms within the molecule. This can provide a richer spectrum, with a more detailed compound specific fingerprint than UV.

In one embodiment of the invention, the combination of both NIR and UV-vis can be used to analyze a single sample. Not only will the analysis determine the concentration of the target constituent, it also will confirm that the target constituent is indeed the desired or suspected target constituent. The combination of technologies allows the testing of samples having a broader range of concentrations and constituents. Returning to the example discussed immediately above, if the target constituent is assumed to be Compound A, for example, in an intended concentration, the service provider can use a combination of NIR and UV-vis technologies to confirm that the target constituent is Compound A from its NIR fingerprint and also determine the concentration through the comparison of UV-vis and/or NIR absorbance spectra and the application of the appropriate equation(s) or vice versa, depending upon the characteristics of the target constituent.

In another aspect of the invention, the method includes the analysis of samples of unknown concentration or purity for the presence of contaminants, including microbial, endotoxin and particulate matter in a mixture of ingredients. These determinations can be made by conventional analyses known to the art or can be a component of spectral absorption or fluorescence analysis. Hence, it is another aspect of the invention that the system can perform UV-vis and/or NIR absorbance and/or fluorescence or any combination thereof.

By way of example, the presence of particulate matter and other contaminants can be determined by such processes as microscopic identification and/or light obscuration. Contamination by microbial organisms can be identified through the traditional methods, such as microbial identification by propagation in appropriate microbial media and under appropriate environmental conditions, or by determining the presence of ATP resulting from bacterial respiration using spectral and/or chromogenic means, or by determining the presence genetic material from undesired sources including but not limited to bacterial, fungal, yeast, viral, plant or animal. Endotoxins can be identified using traditional test methods such as the rabbit test, gel clot test, kinetic or endpoint chromogenic or turbidometric methods, or by using recombinant technologies, or by other spectrophotometric means.

One aspect of the invention is a method of analysis of a compounded product prior to administration of the product to a recipient.

Figure 5:
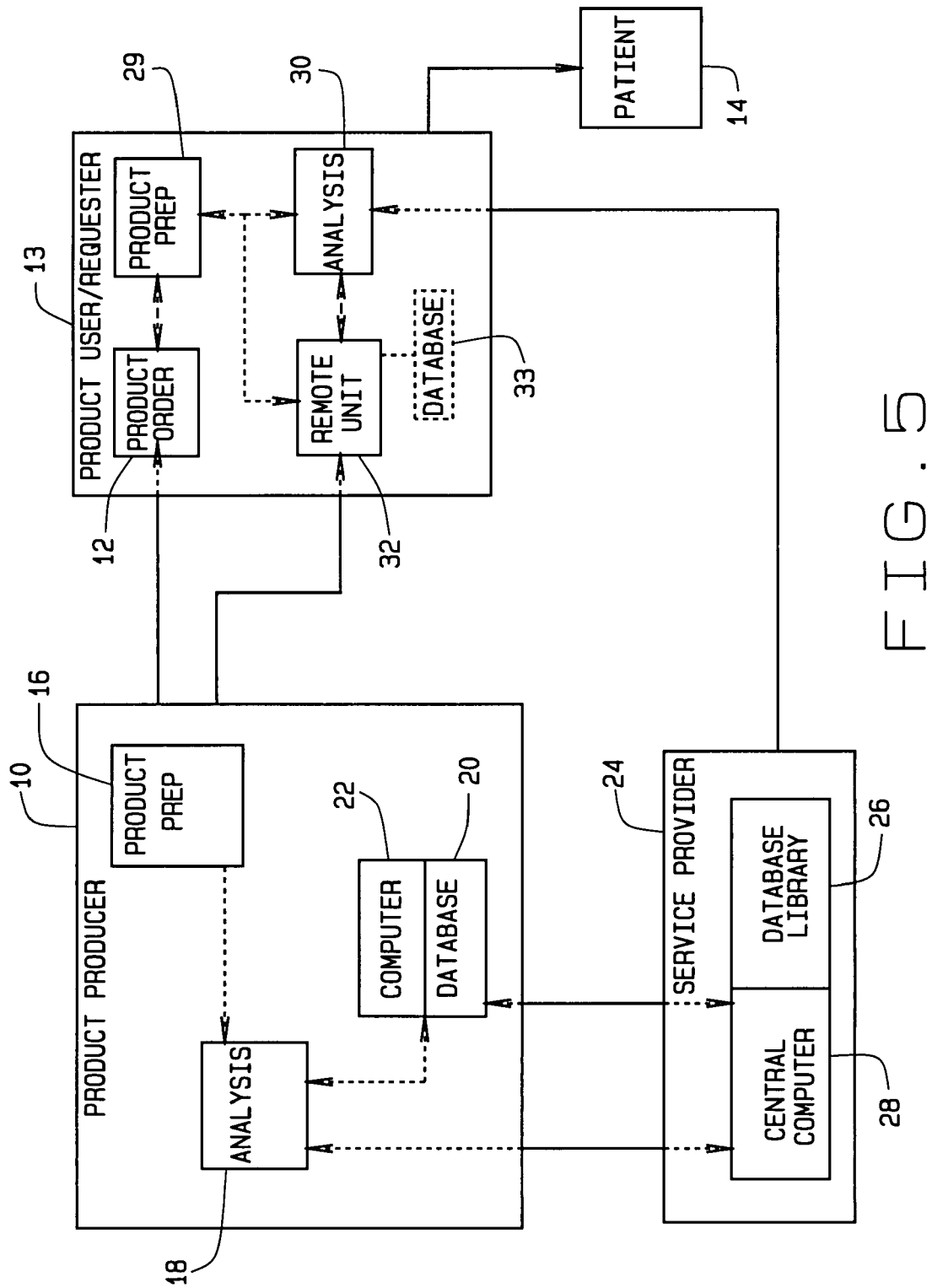
FIG. 5 is a block diagram illustrating one exemplary embodiment of a method of the present invention.

In one aspect of the present invention, illustrated generally in FIG. 5, a product provider 10 receives requests for a product or a product order 12 having a desired concentration of a target constituent, for example, a desired concentration of a chemical, drug or pharmaceutical. These requests generally come from a prescriber, such as a physician, or a user, for example a caregiver such as a nurse, referred to in the example as a product user/requester 13, often located at a site remote to the product provider 10 and nearer the recipient of the sample, such as a patient 14. Stated differently, the product provider 10, such as a pharmacy, receives a product order 12 or prescription for a compounded pharmaceutical from a product user/requester 13 to be administered to a patient 14.

In one aspect of the invention, the product provider 10 prepares the product 16 in response to the product order 12. The product may be compounded extemporaneously or taken from a bulk supply of previously compounded product having the desired concentration of target ingredient. In any event, the product provider 10 compounds or admixes the product to be administered to the patient 14 according to the request or product order 12 received.

In one aspect of the invention, the product provider 10 can then run a spectral analysis 18 of the product, either by using UV-vis spectroscopy, NIR spectroscopy, or a combination of both. The spectral data of the sample obtained from spectral analysis 18 is compared to a database 20 of stored spectral data for that target constituent to determine the concentration or purity of the sample through the comparison. The determination made through the comparison and application of the appropriate equation, as described above. Analysis 18 can be performed by the product provider 10 using the apparatus and techniques described above and also as described in co-pending application Ser. No. 11/051,419, filed Feb. 4, 2005, which is incorporated herein by reference, or by the use of a remote or handheld unit of a type to be described below.

The product provider 10 can develop and maintain a library of spectral data of samples of known constituents, concentrations and purity stored in a retrievable format in database 20. It will be appreciated that database 20 generis operatively associated with a computer such as computer 22. The database 20 can be physically maintained at any site, such as a remote or portable computer as well as computer 22, which may be located on the product provider's site, for example, in a pharmacy.

The product provider 10 also may provide, determine or obtain the spectral data of samples to store in the database 20. In another aspect of the invention that service may be provided by a service provider 24. In one aspect of the invention, a database 26 is maintained in a central computer 28 by a service provider 24. The service provider's computer 28 and database 26 can be operatively associated with the product provider's computer 22 and database 20 or can be independently accessed. The product provider 10 database 20 or the service provider 24 also can obtain spectral data to store in their databases from third parties or regulatory agencies (not shown). It will be appreciated that the databases are constantly expanding.

In one aspect of the invention the product provider 10 performs spectral analysis 18 using the NIR or UV-vis measurement techniques, or other techniques such as fluorescence, nephelometry, turbidity, laser light scattering, dna sequencing, Raman, mid-infrared (IR), TD-NMR, TeraHertz, x-ray, described above, and obtains spectral data from samples having a known concentration or purity.

Furthermore, the product provider 10 can perform the tests for contaminants, including microbial, endotoxins and particulate matter in a mixture of ingredients. The data from the sterility and purity testing is stored in a retrievable form in computer 22 and/or associated database 20 or the database 26 maintained by a service provider 24.

The product provider 10 can confirm that the target constituent is indeed the intended target constituent based upon the unique spectral fingerprint of the constituent based upon the analysis 18 performed, as explained above.

The product then is transported to the requester/user 13 for administration of the product to the recipient or patient 14. At this point, the product may be administered to the recipient since the contents and purity were confirmed by the product provider 10.

In another aspect of the invention the confirmation of the contents and purity of the product are confirmed by the requester/user 13 by analysis on-site or nearer to the point of administration if the user/requester 13 wants to confirm the contents and purity of the provided product, using a portable apparatus.

Alternatively, the user/requester 13 may need to prepare a product on-site, that is at site different from, or remote from, a product provider's site, such as a nursing station or patient's bedside, and confirm the contents and purity of the product as prepared on site. In such a situation, for example, the user/requester 13 may receive a product order 12 on site or may initiate a product order. The product is prepared on site, as at 29. Typically this could occur if there is an emergency order or there is not time to procure a compounded product from a product producer 10.

Whether the product/user requester is performing an analysis 29 to confirming the contents of a product provided by a product producer or analyzing a product prepared by the product user/requester, the product user/requester employs a portable apparatus such as remote testing unit 32 that generally is operatively associated with the computer 22 and data base 20 operated by the product provider 10. In another aspect of the invention, the remote testing unit 32 may be operatively associated with the computer 28 and database 26 operated and maintained by a service provider 24. Or the remote unit can be operatively associated with both computers and databases. In another embodiment, the remote unit may include a computer and database 33. Various embodiments of remote testing apparatus used to perform analyses on site will now be described in greater detail. It will be appreciated that the remote unit may also be referred to as a mobile unit, portable apparatus, a remote system, a hand-held unit, a portable unit, a bedside unit or may be referred to as an instrument, such as a portable instrument or hand-held instrument. In any event, such a remote unit is intended to encompass an analytical instrument of the present invention which is of an appropriate size to allow its use at a non-centralized site. Preferably the remote unit is portable and can be used at multiple sites.

FIGS. 6 through 13E illustrate various aspects of the present invention, which comprises apparatus and method for performing the above-described analyses on-site. That is, the analysis can be performed at the site of compounding or administration of the compounded products. For example, the analysis can be performed in a pharmacy, on a hospital floor or even bedside.

One aspect of the present invention broadly provides for at least two spectral measurement apparatus. These include a base unit, or pharmacy unit, where the primary information on the medication is recorded, and a portable apparatus, most likely in a handheld form that can be used by the nurse or caregiver prior to administering the medication, and which is indicated generally by FIGS. 6-8. It will be appreciated that a base unit could be located in another central location, such as a service provider's location. The service provide could provide the service of building, maintaining and storing a database of known spectral data for access by a mobile unit, without necessarily engaging in the services of compounding and dispensing medications, as the pharmacy or other product provider would.

In any event, whether the base unit is housed in a pharmacy or service provider both, for example, the base unit and the portable apparatus include identical spectral measurement technologies, and identical measurement platforms so that an accurate comparison between the spectral signatures can be obtained. The base unit can include additional functions such as formulation validation, particle detection and measurement, and sample sterility measurements (by detection of certain biological agents). In one aspect of the invention laser light scattering technology is used for particle detection. Tagging agents are used to detect the presence of specific biological agents.

A preferred aspect of the invention is to provide portable apparatus that allows accurate measurements at relatively short optical channels or path lengths that receive the sample. The pathlength is determined by the concentration of the target constituent, e.g. the medication in the sample. The pathlengths are optimized to provide of a spectrum of optimum intensity within a range of approximately 0 to 1.5 absorbance for good linearity and sensitivity. Absorbance being the absorption of energy at a specific wavelength or frequency by the sample. Absorbance is the unit of measure of absorption intensity. If the concentration is high, a shorter path length is used. If the concentration is low, a longer path length is employed. By way of example, a path length of approximately 0.025 mm might be used for a sample having a concentration of 20 mg/ml. These relatively short path lengths require only a minimal amount of sample, for example from a syringe, that only requires a single step in transferring the sample into the apparatus, and only requires a single "push of a button" for the final measurement. The apparatus includes the use of a micro-spectrometer-based spectral measurement technology that covers the spectral range from approx. 200 nm to 1100 nm (UV to NIR). This can include two micro-spectrometers operating in tandem, covering the ranges of 200 nm to 700 nm and 600 nm to 1100 nm. In either case, an optimized series of sample slides, cells or plates with a common method of sample introduction point is employed that provides optimized path lengths for the different spectral regions, so that a single sample can be taken for all the acquired spectral data.

Figure 6:
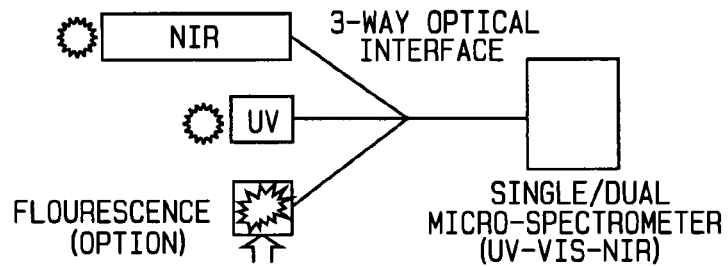
FIG. 6 is a schematic drawing of an example hybrid-spectral measurement system of the present invention.

FIG. 6 illustrates schematically one embodiment of an apparatus featuring UV-visible, NIR and fluorescence-based spectral measurement technology. In this example three sample cell formats are used based on a common 1 cm profile of sample slide. Up to three separate illumination sources are linked via a common optics, which can be optical fiber-based, to one or two common spectrometers. This is just one of several configurations that can be used. With the configuration shown in FIG. 6, the individual optical channels are switched by selecting the individual sources. A common single micro-spectrometer may be used for each of the measurement ranges.

Alternatively, the apparatus can use two micro-spectrometers, one for the NIR and one for the UV-visible (including the fluorescence option). Data is acquired from example medication systems based on placebos that model the response of common medications and common medication formulations. The objective is to span the range of common material types, and the most frequently used concentration ranges to provide example response data for the 2-/3-channel system. A standard PC is used for data collection, using acquisition software developed for the micro-spectrometer.

Figure 7A:
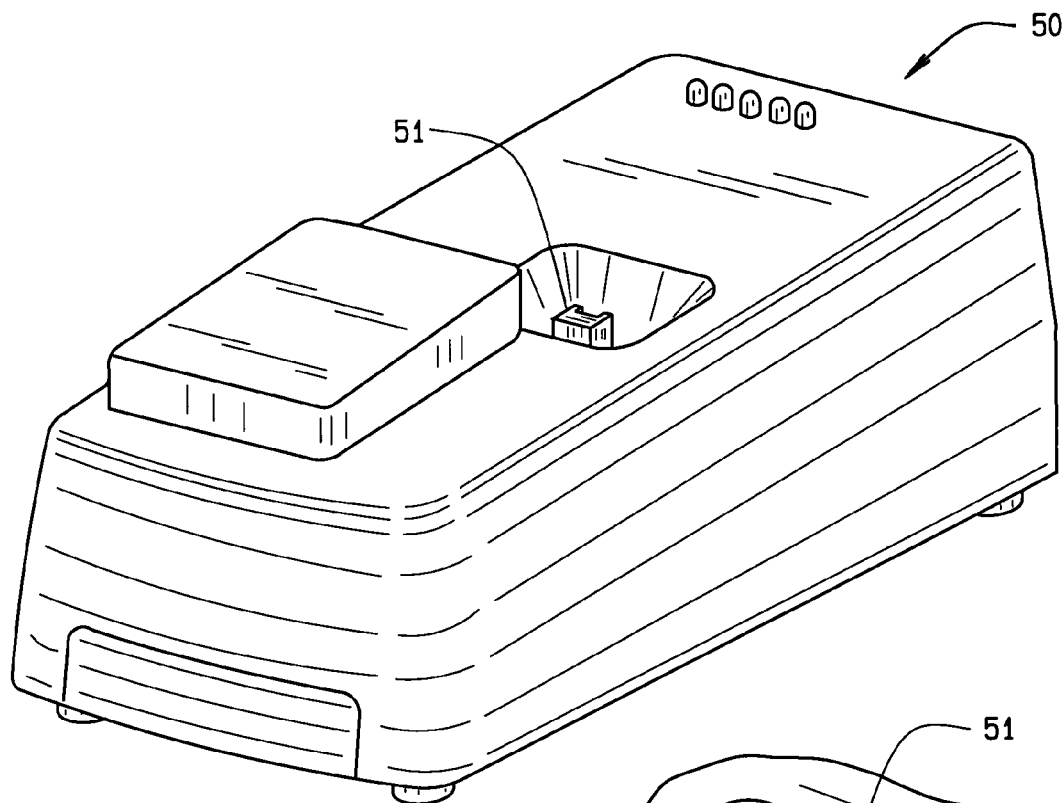
FIG. 7A is a perspective view of an example embodiment of a portable instrument of the present invention.
Figure 7B:
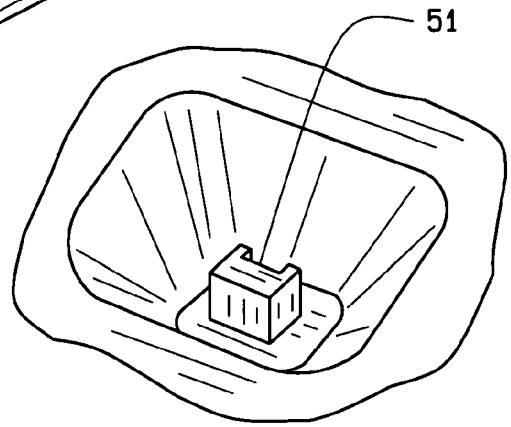
FIG. 7B is an enlarged perspective view of the sample slide of FIG. 7A.

FIG. 7 provides an overview of one representative embodiment of a portable apparatus, indicated generally by numeral 50. The apparatus features fiber-optic couplings, internal fiber-optic cables (not seen), the optimized sample slide, cell or plate 51, the source electronics and some of the driver software. In this example version, the user interface and data entry is manual, and this is implemented via a PDA, such as the original Compaq iPac PDA platform, which is available as an OEM component.

One representative embodiment includes a micro-spectrometer (possibly two units) within a simple enclosure. It features two light sources in an integrated package: one UV source (such as a deuterium lamp) and one tungsten source for the visible/NIR range. Single or dual spectrometer configurations will work for the application both operating via a USB interface. The apparatus preferably includes a rechargeable battery power supply with smart power management to enable power levels to be monitored. The portable apparatus can stand-alone, without the need for external computer support. However, the option to couple to an external PC is included for Ethernet or USB or standard serial-based communications.

Representative 1-cm sample slides 51 are shown in FIGS. 8-8C. This component can be machined to provide sample channels or path lengths varying from about 0.01 mm to about 10 mm. Another preferred embodiment is molded, for example, from a rigid optical polymer, such as an acrylate or a polycarbonate.

The optics employed in apparatus of the present invention are non-traditional. The optics are designed to reduce down the imaging to accommodate small sample volumes. It is preferred to use only a minimal amount of the sample to be analyzed without any significant consumption of the dose. In order to do this the sample image is reduced down to the field of view of a 600 micron fiber optic. This is imaged through a collimator to give an overall sample image size (diameter) of 3 mm max. This amount can be contained in the sample slide. This minimizes the sample volume depending on the strength on the sample.

The invention employs four different path lengths handling the range of dosage concentrations. The path length is the distance traveled by the light/energy through the sample and comprises an optical channel that holds the sample. The sample to be analyzed is introduced into the optical channel in the sample holder. Hence, there is a direct relationship between the sample size (volume) and the path length (optical channel) for a given channel cross-section. The present invention employs spectral measurement technology that allows accurate spectral measurement as a function of a defined path length or sample size. The present invention provides for accurate measurement of very small volumes of samples. This feature allows for a portable apparatus as well as conservation of sample. The illustrated embodiments include configuration that provide path lengths over the range of about 0.025 mm to about 10 mm. A maximum path length, for example approximately 10 mm is used for the NIR measurements and for low dilution UV-visible measurements. The very short path lengths are intended for UV-visible measurement from the highest concentration solutions. Representative path lengths and sample volumes are as follows:

| | | |
|---|---|---|
| 10 mm | Sample volume: | 70.7 microliters |
| 1 mm | | 7.07 microliters |
| 0.1 mm | | 0.7 microliters (700 nanoliters) |
| 0.025 mm | | 0.175 microliters (175 nanoliters) |

The samplers, i.e. the optical channels can be self-filling via capillary action, except for the larger 10 mm size. Alternatively, samples can be introduced into the sample channels by acceptable means such as injection.

The apparatus operates with a approximate signal-to-noise ratio in the range of 1000:1 to 10,000:1, and with an approximate measurement time frame of between approximately 0.1 and 1.0 minute.

The apparatus preferably includes a single light source unit that generates radiation from 200 nm to 2500 nm. This is a compact light source with integrated optics and takes up less space than a single light source. It does not require beam switching; the source is continuous in terms of the range covered.

The apparatus of the present invention preferably is hard coupled providing optimum light coupling between the spectrometer and the light source. This makes the apparatus more compact and it is more efficient than traditional optics. There are no mirrors or lenses involved which is different other instruments. Not only is this more efficient, but there are no alignment issues. The apparatus maintains alignment at all times, making it a truly portable analytical instrument.

The apparatus of the present invention is operated by programmed software to carry out the necessary operational and spectroscopic functions, as will be understood by one skilled in the art. Such software, for example, is written for the Windows CE operating system in, VB6, VBnet, C++ or a comparable development language. The apparatus can incorporate a standard OEM PDA-style computer platform. The apparatus employs electronics that include the basic requirements to drive the spectral measurement systems, to do the necessary data manipulations, and to provide external communications—both hardwire networked and wireless.

The described methods can be used to analyze compounded sterile pharmaceuticals (CSPs) or non-sterile compounds, as set out. However, it will be appreciated that the methods of the present invention can be used to analyze the concentration or purity of other substances or compounds without departing from the scope of the invention.

As one skilled in the art will appreciate, the order of the steps of the methods described herein is not critical. The method steps described may be performed in various orders. More over, the steps may be performed at different times, for example, the steps of determining spectral data of a concentration or purity of a sample having a known concentration or purity or storing in a database the spectral data of a concentration or purity of a sample having a known concentration or purity may be performed well in advance of other of the steps. Moreover, steps such as these may be performed once only, while others of the steps performed for each new requested analysis.

Figure 10:
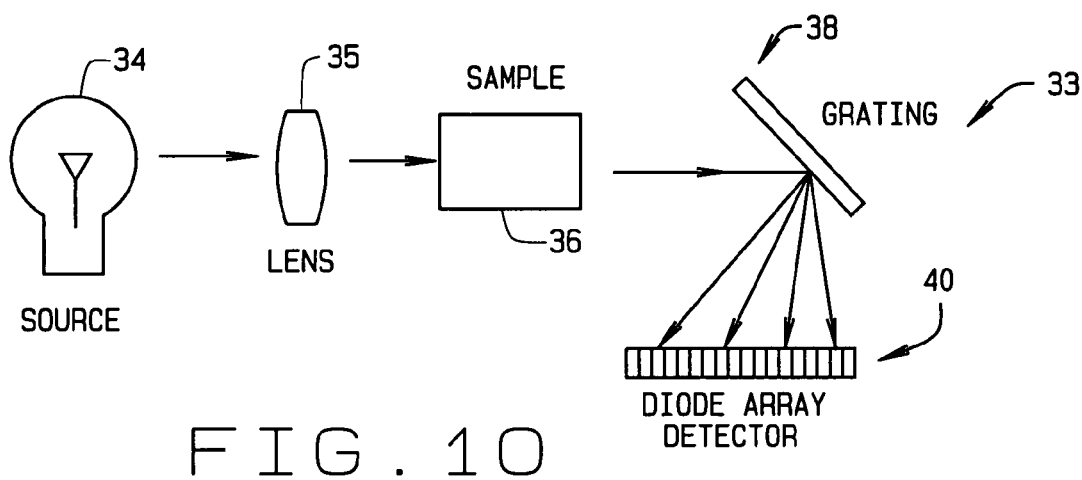
FIG. 10 is a schematic drawing of a grating-based diode array spectrometer arrangement for providing an on site analysis of the present invention
Figure 11:
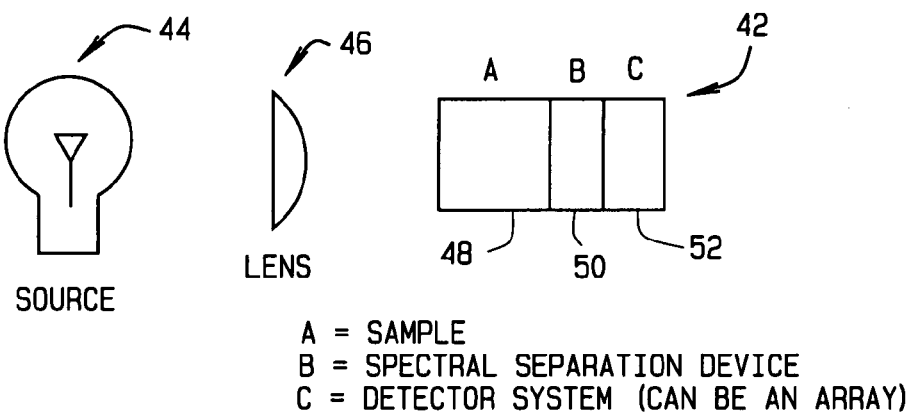
FIG. 11 is a schematic drawing of alternative spectrometer format where optical spectral separation provides the necessary discrimination for an on site analysis within the present invention.

In general, the apparatus employed in the present invention incorporates multi-level spectral measurements that include measurements made in the ultraviolet (UV), visible, or near infrared (NIR) spectral regions. For reference, these spectral regions are defined as covering the following wavelength regions: 200 nm to 400 nm (UV), 400 nm to 700 nm (visible), and 700 nm to 2500 nm (NIR). The UV and Visible are commonly combined and referenced as UV-vis, Another illustrated embodiment of an apparatus for analyzing the sample on site is indicated schematically in FIGS. 10 through 12. The apparatus comprises a spectral measurement system, indicated generally by reference numeral 33 in FIG. 10 for the analysis of a sample. As shown, the apparatus comprises an energy source 34, interfacing optics 35, a sample interface 36, which is generally, a cuvette or an equivalent disposable device, and a spectral analysis system capable of producing a spectrum characteristic of the material under study. The portable device illustrated in FIG. 10 is a diode array spectrometer that features a diffraction grating 38 for the method of energy/spectral separation. The apparatus includes a diode array detector 40. This invention is not limited to this format of measurement system, and alternative embodiments are to be considered. FIG. 11, indicates another general embodiment of a portable instrument 42, which can include various methods of wavelength tuning or wavelength separation. These can include, but are not limited to spatially selective optical filters, tunable filters (such as tunable Fabry-Perot etalons), tunable light sources (such as tunable solid devices), Michelson interferometers, and other optical measurement concepts. For example, apparatus 42 of FIG. 11 includes an tunable energy source 44, optical filter such as lens 46, a sample holder 48, a spectral separation device 50 and detector system 52.

Figure 9:
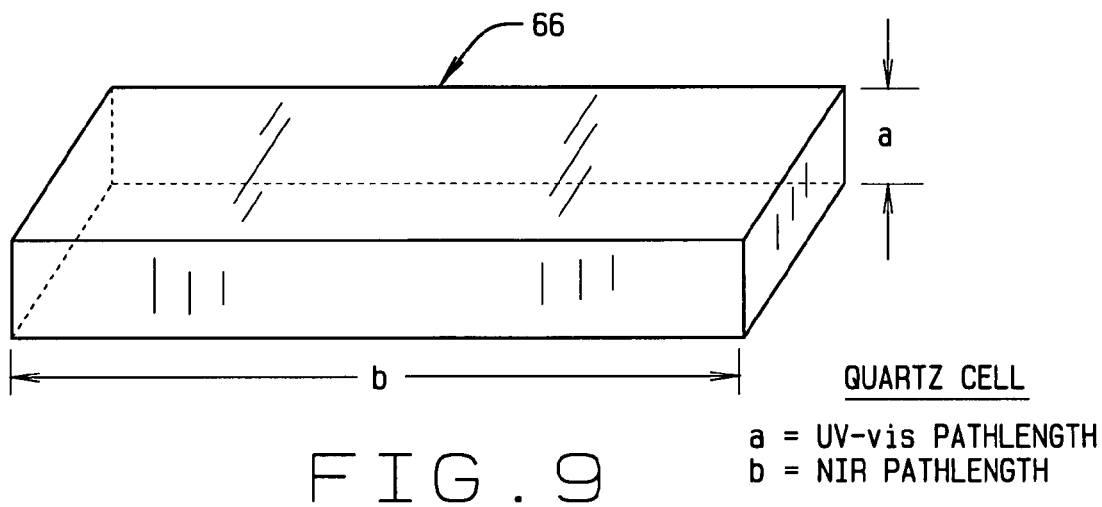
FIG. 9 is an enlarged drawing of an example quartz sample cell indicating the path lengths for NIR and UV-vis energy.
Figure 12:
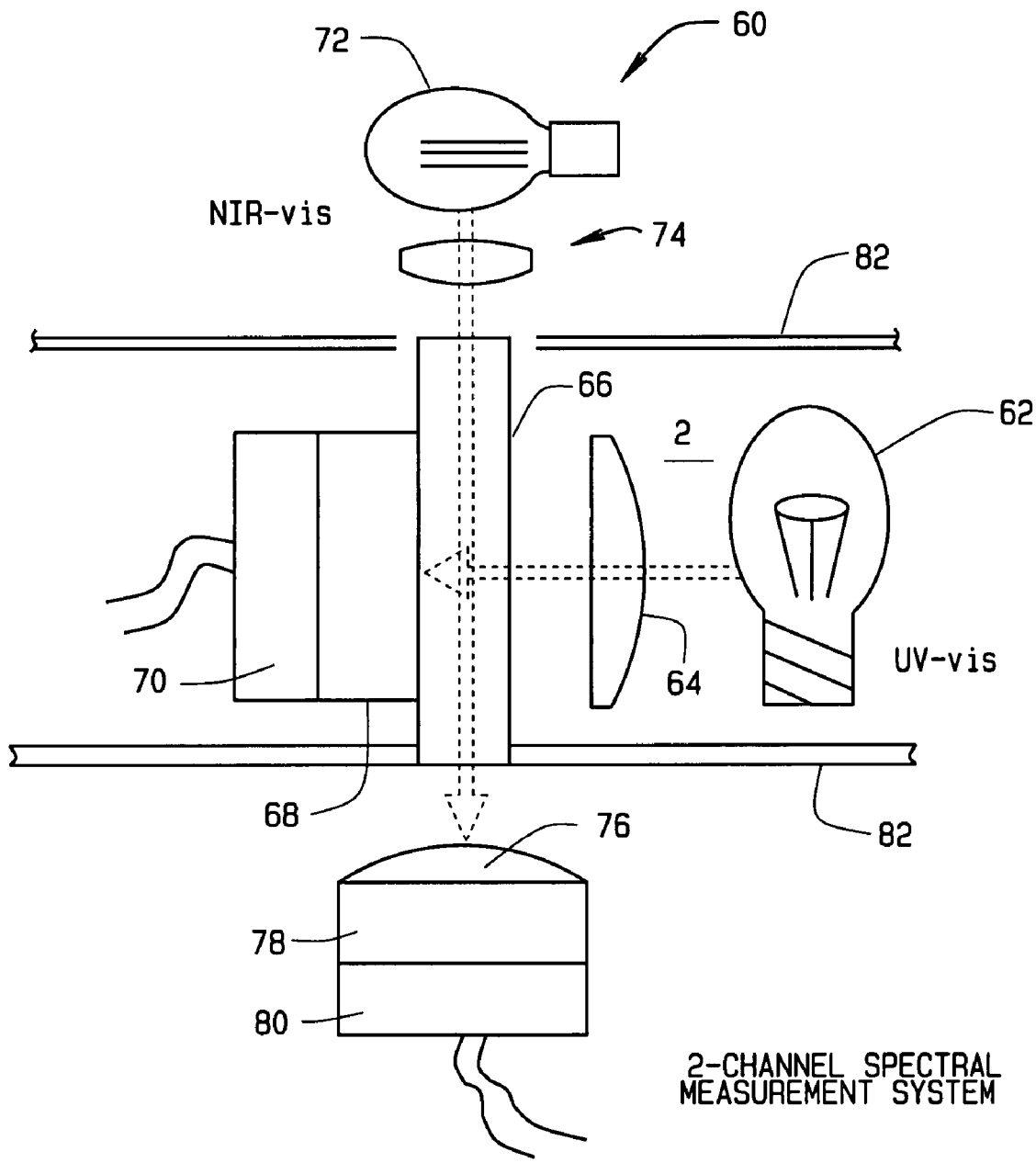
FIG. 12 is a schematic representation of a preferred embodiment of a portable analysis device of the present invention including UV-Vis and NIR measurement systems.

In a preferred aspect of the invention, a portable apparatus, indicated generally by reference numeral 60 in FIG. 12, includes spectral measurement technology for performing a spectral measurement in more than one spectral region. As illustrated, apparatus 60 comprises a composite UV-vis light source 62, a collimating lens 64, and a sample cell 66. FIG. 9 illustrates an example quartz sample cell 66, which is configured for two wavelength regions, with the NIR path length, indicated by dimension a, of about 1.00 cm or longer and the UV-vis path length, indicated by dimension b, of about 0.01 mm to 10.0 mm. The path lengths quoted are for example only, and in all embodiments of the invention, the cell/sample slide and apparatus is optimized for the measurement systems and the expected range of sample concentrations.

Apparatus 60 also comprises a UV-vis diode array spectrometer indicated by 70 and wavelength separation component 68. Apparatus 60 further includes a NIR-visible source 72, an imaging optic 74, normally a lens, but it could be a focusing mirror, interfacing optics 76, a spectral separation element 78, such as a grating spectrometer and suitable spectral measurement system capable of producing a spectrum characteristic of the material under study. The latter can also be a diode array spectrometer. The portable unit includes a light-tight enclosure 82.

Portable apparatus 60 is intended to be operated stand-alone. It can be connected to a main computer for up-loading or down-loading data or software via USB or similar interface cable or wireless, for example using IEEE 802-11 b or other standard wireless technology. The apparatus is appropriately sized and the components just described encased in an appropriate light blocking material 82. Apparatus 60 can measure UV-vis absorbance of each of samples in the range of about 200 nm to about 700 nm (the specific range for UV would be 200 to 350 nm) and NIR in the range of about 700 nm to about 1100 nm.

FIGS. 13A-13E illustrate yet another aspect of the invention. The apparatus used for the measurement, features a special sample holder 70 that accepts sample slides that are optimized for light throughput and minimization of sample consumption. The holder 70 may include two additional optical channels. A first channel 72 provides the option to excite the sample with a specific wavelength normal to the analytical channel and to measure fluorescence of the sample within the analytical channel. This fluorescence may be native to the sample and may be characteristic of materials used in the admixture. Alternatively, the fluorescence may be induced by the addition of a specific chemical reagent that is added for the purpose of inducing fluorescence as a consequence of the presence of one or more endotoxins or similar biological agents or microbials. The reagent added is specific and provides a unique fluorescence (resulting in one or more emissions of specific wavelengths). The spectral analysis of the signatures produced is used to characterize the agents concerned plus the concentration of the materials. An additional second optical channel 74 mounted normal to the analytical channel features a laser back scatter assembly comprising of a bifurcated fiber optic cable (FIG. 13E) featuring laser excitation in one channel and optical emission detection as a result of particulate backscatter in the return fiber channel. This configuration provides information on the presence of particulate matter. The apparatus features a sampling block that provides access to the three channels defined; the main analytical channel (used for UV-vis-NIR) 72, the fluorescence excitation channel 74 and a laser illuminated channel 76. Three formats of a disposable sample slide are used to enable three modes of operation. A combination of the spectral data, the induced fluorescence data and the particulate data enables the system to provide a full signature of dosage potency and purity for any given sample.

Although not shown, apparatus includes appropriate digital or LCD displays or similar components, to allow visualization of the reported data to the user.

The portable apparatus of the present invention is designed to accept a small volume of sample liquid and determine or confirm the identity and/or purity of the sample. The apparatus includes the appropriate electronics to control the instrument, collect and relay a signal from the detectors and communicate with a separate computer. The associated computer is appropriately programmed to analyze and compare the spectral data obtained from the on-site analysis to the database of spectral data stored in the computer, as earlier described. The computer transmits back to the apparatus, in readable form, the results of the analysis. In other aspects of the invention, the remote testing unit may include an appropriately programmed computer and associated database.

Analysis of the data is performed by appropriate qualitative and quantitative software employing one or more of the following algorithmic approaches, vector matching tools such as dot product and/or Euclidean distance, Mahalanobis distance, principal component analysis, conformity index, polar coordinates and/or spectral matching, for example. Another aspect of the invention comprises qualitative and/or quantitative software for assay value employing Beer's law, linear and non-linear 2-D calibrations, multiple linear regression, partial least squares, principal component analysis, Mahalanobis distance, and/or neural networks, for example. The apparatus also employs appropriate software to prepare spectra for analysis including smoothing, derivatives ($1^{st}$, $2^{nd}$ $3^{rd}$ and $4^{th}$): both Norris and Savistsky-Golay, single normal variant, multiplicative scatter correction, baseline adjustments and normalization, as examples.

Derivatives are one form of data conversion used to help extract information from a spectrum. In the case of UV-visible and even NIR data derivatives are used, generally first or second derivative, to help extract data from a spectrum that would be otherwise obscured by spectral overlap. The derivative processes help to narrow the spectral features and help make the hidden data more readable. Higher orders, and sometimes $3^{rd}$ or $4^{th}$ derivatives can be used but are limited by the signal-to-noise performance of the spectral measurement system, and the noise level in the recorded data. Derivatives are used when comparing and assessing dilute solutions, where the active component is a minor ingredient. In this way methods of the present invention are able to assess minor components in a medication formulation. However, preferably the method employs $1^{st}$ or $2^{nd}$ derivative.

Another aspect of the invention that incorporates a portable apparatus of the present invention comprises an automated measurement system that records the quality and identity of the medication produced at the pharmacy, and then further confirms that it is the exact same medication that is being delivered to the patient. This is accomplished by producing a spectral signature of the material on a spectral measurement system located at the pharmacy. This signature will be recorded on a hybrid instrument that incorporates multi-level spectral measurements that include measurements made in the ultraviolet (UV), visible, and near infrared (NIR) spectral regions. This information is stored within a database. Once a prescription is produced for a patient, a patient identifier is assigned, and in turn, the spectral signature of the medication is linked to that specific patient. While the system can be used to analyze medications in an injectable form, most liquid medications can be analyzed, and solids may be analyzed if dissolved in a suitable solvent/medium.

The confirmation of the delivery of the correct medication and dosage to the patient is made at the bedside from a portable apparatus operated by the caregiver administering the medication. The portable apparatus performs the same analysis or measurement made in the pharmacy, and compares the resultant signature with the spectral signature of the medication assigned to that patient that is stored in the database. A matching algorithm is used to compare the two sets of spectral data. With a statistically relevant match, the handheld unit will signal to the caregiver that it is acceptable to administer the medication to the patient. The information is relayed in real time.

One embodiment uses at least two levels of spectral information to confirm a specific medication which include, at minimum, UV-vis and NIR spectral signatures, such as those previously described, which reflect information from both the active pharmaceutical ingredient(s) and any excipients. As indicated the spectral region includes the visible spectrum so that any spectral contributions from color centers can be included. An additional level of spectral signature characterization that can be analyzed as part of the overall signature is fluorescence. The latter information is useful for active ingredients that are known to have strong fluorescence signatures, and also for detecting contamination. Fluorescence also can be employed as a supplemental tool for assessing sterility.

The foregoing represents the best mode of carrying out the invention presently contemplated by the inventors. It will be appreciated that various modifications or changes may be made in the foregoing methods and apparatus without departing from the scope of the invention or the appended claim. The description of the invention contained herein is illustrated only, and is not intended in a limiting sense.

What is claimed is:

1. A method of confirming the concentration or purity of a sample of a liquid having a desired concentration or purity, comprising the steps of:
   introducing a sample of a liquid having a desired concentration or purity into a liquid sample channel of a hand-held analytical instrument, said hand-held analytical apparatus comprising apparatus for performing a spectral analysis of the sample in at least two liquid sample channels each having a different path length of about 0.025 mm to at least about 1.0 cm;
   performing a spectral analysis of sample liquid in said sample channel with said apparatus for performing a spectral analysis;
   obtaining data regarding the spectral analysis of the sample;
   comparing the data regarding the spectral analysis of the sample having a desired concentration or purity to spectral analyses of samples having a predetermined concentration or purity stored in a retrievable form;
   mathematically calculating a concentration or purity of the sample having desired concentration or purity from the comparison; and
   confirming whether or not the determined concentration and purity of the sample having a desired concentration and purity is a desired concentration and purity.

2. The method of claim 1 wherein the step of comparing the data regarding the spectral analysis of the sample having a desired concentration or purity to the data regarding the spectral analysis of the sample having a predetermined concentration or purity stored in a retrievable form further comprises the step of comparing the data regarding the spectral analysis of the sample having a desired concentration or purity to the data regarding the spectral analysis of the sample having a predetermined concentration or purity stored in a compiled database of determined spectral analyses of samples having a predetermined concentration or purity.

3. The method of claim 2 wherein the step of performing a spectral analysis of sample having a desired concentration or purity is performed at a site remote from the compiled database of determined spectral analyses of samples having a predetermined concentration or purity.

4. The method of claim 1 wherein the step comparing the data regarding the spectral analysis of the sample having a desired concentration or purity to spectral analyses of samples having a predetermined concentration or purity stored in a retrievable form is performed through an electronic medium.

5. The method of claim 4 wherein the electronic medium is selected from a group of electronic media consisting of direct electrical interfacing, telephonic transmission, wireless communications, and Internet, including WIFI networked communications.

6. The method of claim 1 wherein the step of performing a spectral analysis of a sample having a desired concentration or purity further comprises performing a spectral analysis of a sample in a sample channel having a path length of about 10.0 mm to about at least 1.0 cm using NIR energy absorption technology.

7. The method of claim 6 wherein the step of performing a spectral analysis of a sample having a desired concentration or purity further comprises performing a spectral analysis of a sample having a predetermined concentration or purity using NIR energy absorption technology.

8. The method of claim 1 wherein the step of performing a spectral analysis of a sample having a desired concentration or purity further comprises performing a spectral analysis of a sample in a sample channel having a path length of about 0.025 mm to about 10.0 mm using UV-vis light absorption technology.

9. The method of claim 1 wherein the step of performing a spectral analysis of a sample having a desired concentration or purity further comprises performing a spectral analysis using fluorescence technology.

10. The method of claim 1 wherein the step of performing a spectral analysis of a sample having a desired concentration or purity further comprises performing a spectral analysis technology selected from the group of technologies consisting of nephelometry, turbidity, laser light scattering, DNA sequencing, Raman, mid-infrared (IR), TD-NMR, TeraHertz, x-ray and combinations thereof.

11. The method of claim 1 wherein the step of performing a spectral analysis of a sample having a desired concentration or purity further comprises performing a spectral analysis of a sample having a predetermined concentration or purity using UV light absorption technology.

12. The method of claim 1 wherein the step of performing a spectral analysis of a sample having a desired concentration or purity further comprises performing a spectral analysis of the sample using NIR energy absorption technology and UV-vis light absorption technology.

13. The method of claim 1 further comprising the step of analyzing the sample having a desired concentration and purity to determine the sterility and purity of the sample.

14. The method of claim 13 wherein the step of analyzing the sample having a desired concentration and purity to determine the sterility and purity of the sample further comprises using laser light scattering technology.

15. The method of claim 1 wherein the sample having a desired concentration or purity is an extemporaneously compounded pharmaceutical preparation.

16. A method of confirming the concentration or purity of a liquid sample having a desired concentration or purity, comprising the steps of:
   performing a spectral analysis of a liquid sample having a predetermined concentration or purity;
   obtaining data regarding the spectral analysis of the sample having a predetermined concentration or purity;
   storing the obtained spectral data regarding the analysis of the sample having a predetermined concentration or purity in a retrievable form;
   introducing a sample of a liquid compound having a desired concentration or purity into a liquid sample channel of a sample cell of a portable analytical instrument, said sample cell comprising at least two different liquid sample channels, each sample channel each comprising a different a path length of between about 0.01 mm to about at least 1.0 cm;
   performing a spectral analysis of the sample having a desired concentration or purity in the liquid sample channel of the analytical instrument;
   obtaining data regarding the spectral analysis of the sample having a desired concentration or purity;
   comparing the data regarding the spectral analysis of the sample having a desired concentration or purity to the data regarding the spectral analysis of the sample having a predetermined concentration or purity which was stored in a retrievable form; and
   determining a concentration or purity of the sample having a desired concentration or purity through the comparison to confirm the desired concentration or purity thereof.

17. The method of claim 16 wherein the spectral analysis of a sample having a desired concentration or purity is performed in a liquid sample channel having a path length of about 10 mm to at least about 1.0 cm in a portable analytical instrument using near-infrared energy absorption technology.

18. The method of claim 16 wherein the spectral analysis of a sample having a desired concentration or purity is performed in a liquid sample channel having a path length of approximately 0.025 mm to approximately 10.0 mm in a portable analytical instrument using ultraviolet-visible light absorption technology.

19. The method of claim 18 wherein the sample is about 0.175 microliters to about 70.7 microliters.

20. The method of claim 16 wherein spectral analysis of a sample having a desired concentration or purity is performed with a portable analytical instrument having at least two sample channels using near-infrared energy absorption technology and ultraviolet-visible light absorption technology.

21. The method of claim 16 wherein the sample having a desired concentration or purity is an extemporaneously compounded pharmaceutical preparation.

22. The method of claim 16 wherein the step of introducing a sample of a liquid compound having a desired concentration or purity into a liquid sample channel of an analytical instrument further comprises introducing approximately 100 microliters or less of the liquid compound having a desired concentration or purity into a liquid sample channel of an analytical instrument.

* * * * *

UNITED STATES PATENT AND TRADEMARK OFFICE
CERTIFICATE OF CORRECTION

PATENT NO. : 7,660,678 B2  
APPLICATION NO. : 11/726417  
DATED : February 9, 2010  
INVENTOR(S) : Russell David Odegard et al.

It is certified that error appears in the above-identified patent and that said Letters Patent is hereby corrected as shown below:

Title Page, (75)

Replace:

"Russell David Odegard (Eureka, MO), Earl Michael Pruett (St. Louis, MO), John Peter Coates (Newtown, CT)"

With:

-- Russell David Odegard (Eureka, MO), Earl Michael Pruett (St. Louis, MO), John Peter Coates (Newtown, CT), Emil Walter Ciurczak (Golden's Bridge, NY) --

Signed and Sealed this

Seventh Day of February, 2012

David J. Kappos  
*Director of the United States Patent and Trademark Office*